(12) United States Patent
Baker et al.

(10) Patent No.: US 12,151,060 B2
(45) Date of Patent: Nov. 26, 2024

(54) RESPIRATORY INHALER CARTRIDGE PLACEMENT TRAINING DEVICE

(71) Applicant: NOBLE INTERNATIONAL, LLC, Orlando, FL (US)

(72) Inventors: Jeff Baker, Orlando, FL (US); Tingting Liu, Orlando, FL (US); Shishuang Hou, Ningbo (CN); Tara Mazzarella, Orlando, FL (US)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 849 days.

(21) Appl. No.: 17/298,746

(22) PCT Filed: Dec. 2, 2019

(86) PCT No.: PCT/US2019/064066
§ 371 (c)(1),
(2) Date: Jan. 19, 2022

(87) PCT Pub. No.: WO2020/113230
PCT Pub. Date: Jun. 4, 2020

(65) Prior Publication Data
US 2022/0054774 A1 Feb. 24, 2022

Related U.S. Application Data

(60) Provisional application No. 62/774,110, filed on Nov. 30, 2018.

(51) Int. Cl.
*G09B 23/28* (2006.01)
*A61M 15/00* (2006.01)

(52) U.S. Cl.
CPC ......... *A61M 15/0001* (2014.02); *G09B 23/28* (2013.01); *A61M 2205/581* (2013.01); *A61M 2205/582* (2013.01); *A61M 2205/583* (2013.01)

(58) Field of Classification Search
CPC ............................. G09B 23/28; A61M 15/009
See application file for complete search history.

(56) References Cited

U.S. PATENT DOCUMENTS 6,358,058 B1 * 3/2002 Strupat ............. A61M 15/0065
434/262
10,391,270 B2 * 8/2019 Adams ................ A61M 15/009
(Continued)

FOREIGN PATENT DOCUMENTS

| EP | 667168 A1 | 2/1994 |
|---|---|---|
| WO | 2017015303 A2 | 1/2017 |
| WO | 2020113230 A1 | 6/2020 |

OTHER PUBLICATIONS

PCT/US2019/64066, Search Report and Written Opinion, Mailed Date Dec. 2, 2019, 8 pages.

*Primary Examiner* — Kurt Fernstrom
(74) *Attorney, Agent, or Firm* — Timothy H. Van Dyke; Wolter, Van Dyke, Davis, PLLC

(57) ABSTRACT

In one embodiment, a resettable respiratory inhaler training device is provided herein. The resettable respiratory inhaler training device includes a device housing having an unlocked position and a locked position, the housing comprising a chamber; a cartridge for placement into the chamber, the cartridge comprising a body for insertion into the chamber and a base, said cartridge including a status indicator window to indicate a new or used cartridge, an aperture in the base and a shutter to selectively open or close the aperture; and a reset cap comprising a protrusion for interfacing with the aperture during reset of the device; wherein operation of the device changes the status indicator window from used to new to reset the cartridge for a subsequent use.

19 Claims, 14 Drawing Sheets

(56) References Cited

U.S. PATENT DOCUMENTS

| | | | |
|---|---|---|---|
| 10,971,035 B2* | 4/2021 | Milton-Edwards | ................................ H04M 1/72427 |
| 11,610,510 B2* | 3/2023 | Baker | ..................... G09B 19/24 |
| 11,715,390 B2* | 8/2023 | Von Hollen | ...... A61M 15/0001 434/262 |
| 2004/0187869 A1* | 9/2004 | Bjorndal | ........... A61M 15/0065 128/200.23 |
| 2015/0320947 A1 | 11/2015 | Eicher et al. | |
| 2016/0148539 A1* | 5/2016 | Baker | ..................... G09B 23/28 434/262 |
| 2018/0092595 A1* | 4/2018 | Chen | .................... A61B 5/1123 |
| 2018/0228989 A1 | 8/2018 | Buck et al. | |

\* cited by examiner

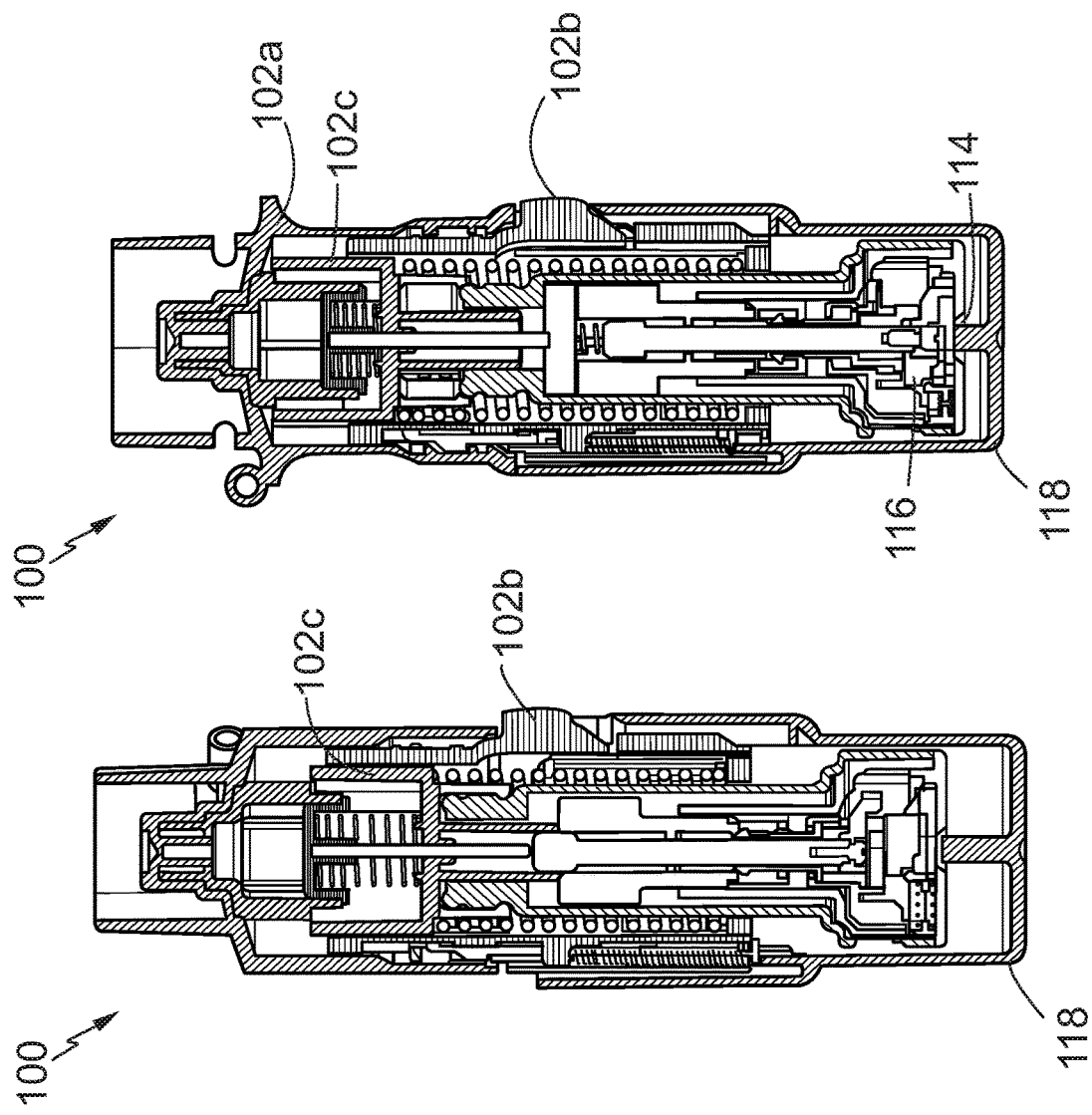

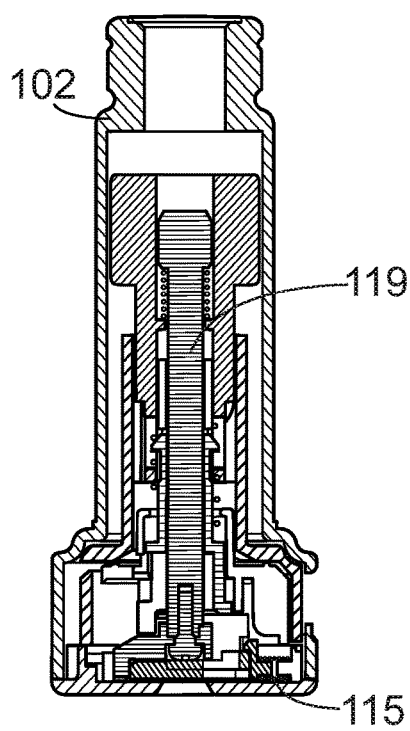
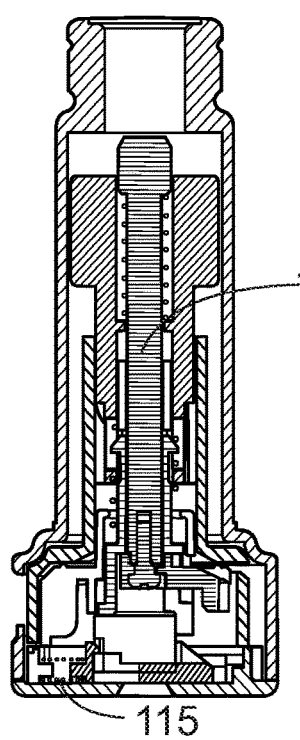
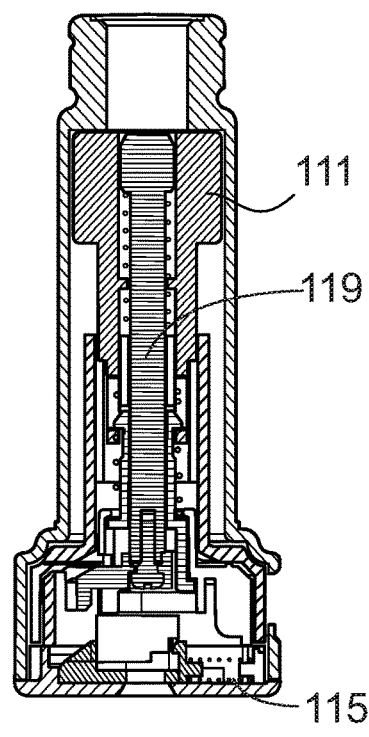
*Fig. 2A*  *Fig. 3A*  *Fig. 4A*
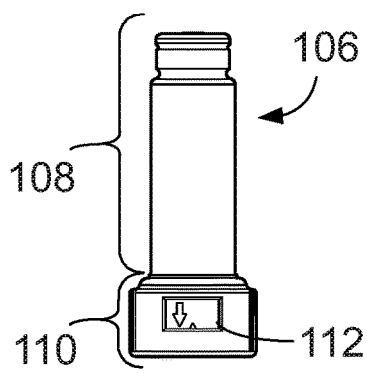
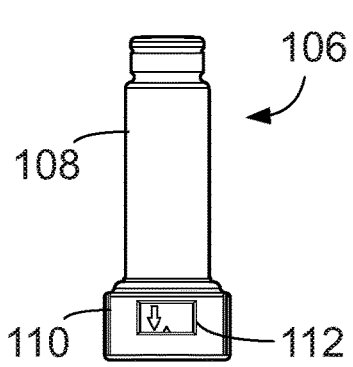
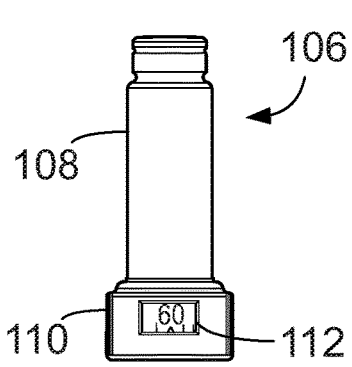
*Fig. 2B*  *Fig. 3B*  *Fig. 4B*
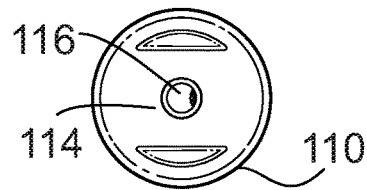
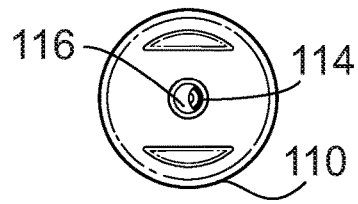
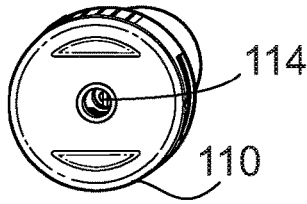
*Fig. 2C*  *Fig. 3C*  *Fig. 4C*

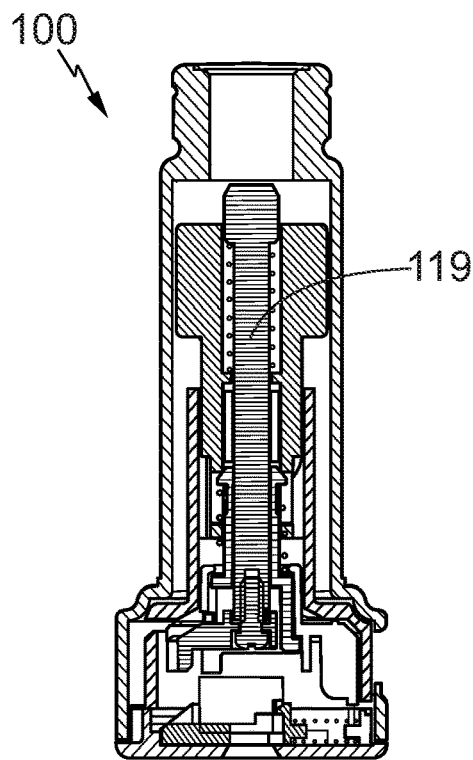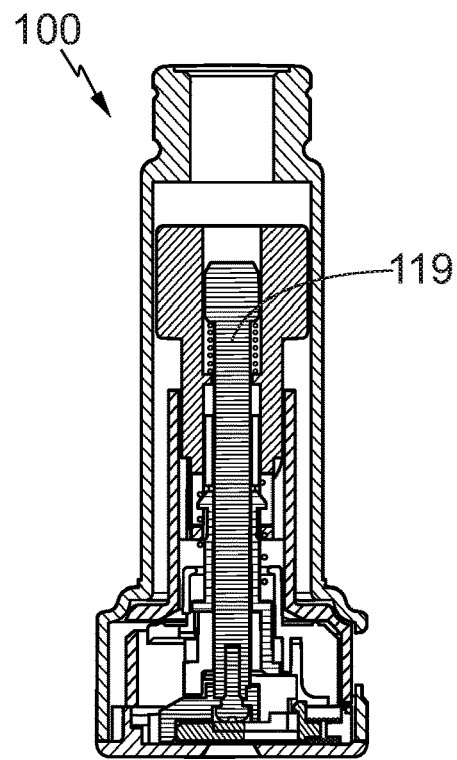
*Fig. 5A*     *Fig. 6A*
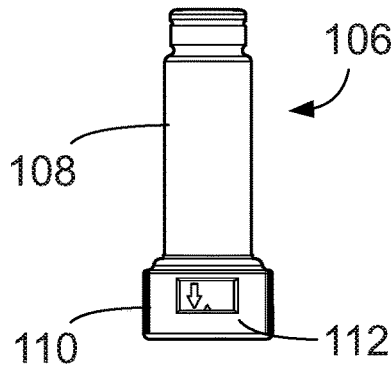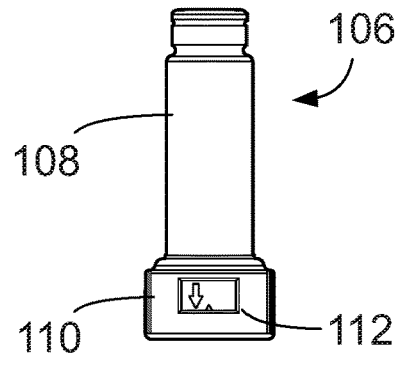
*Fig. 5B*     *Fig. 6B*
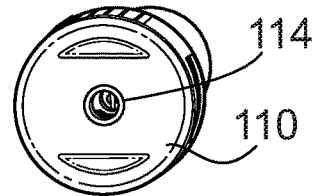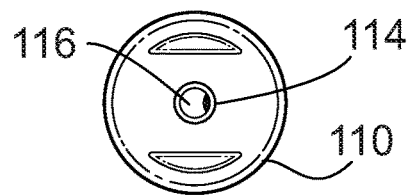
*Fig. 5C*     *Fig. 6C*

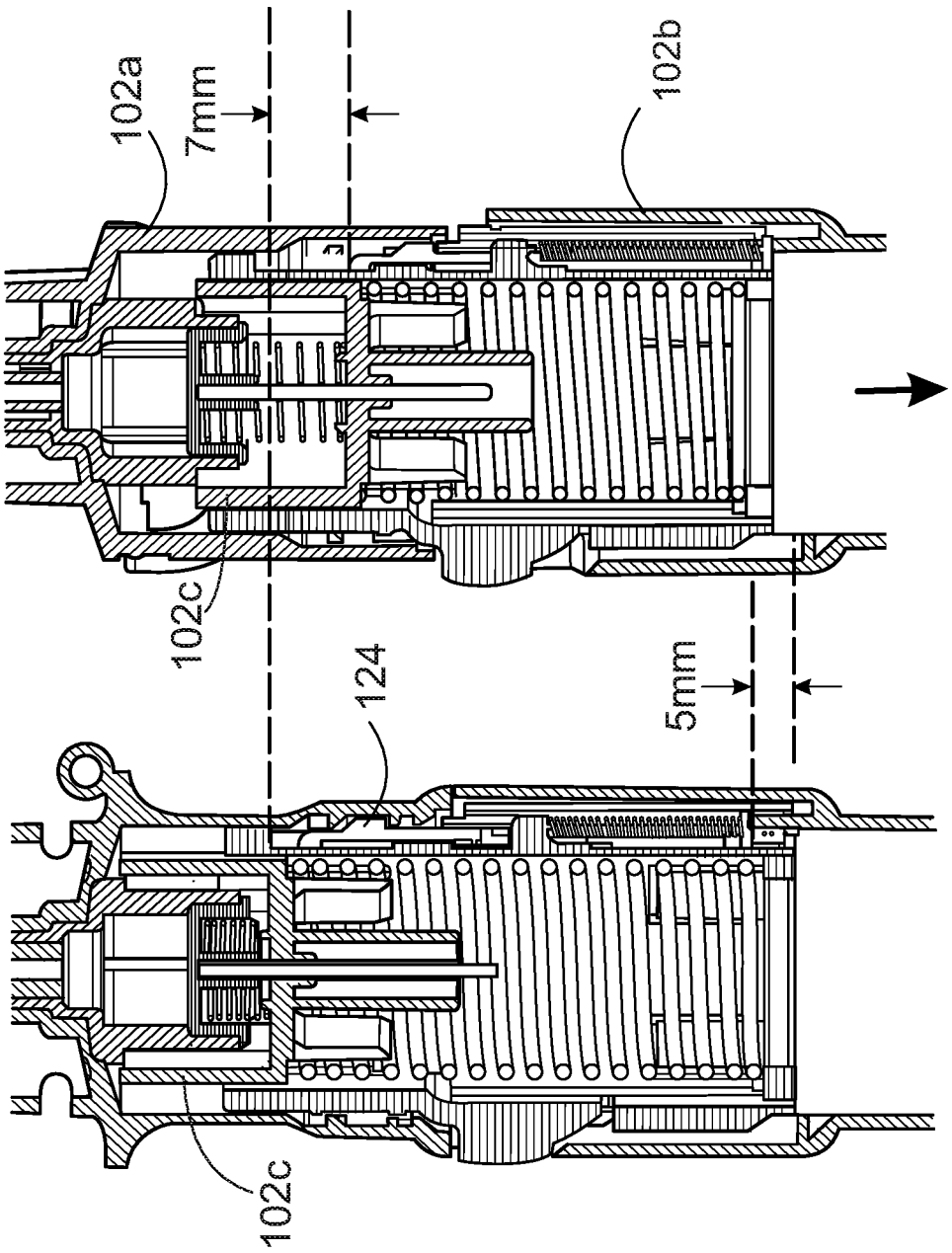

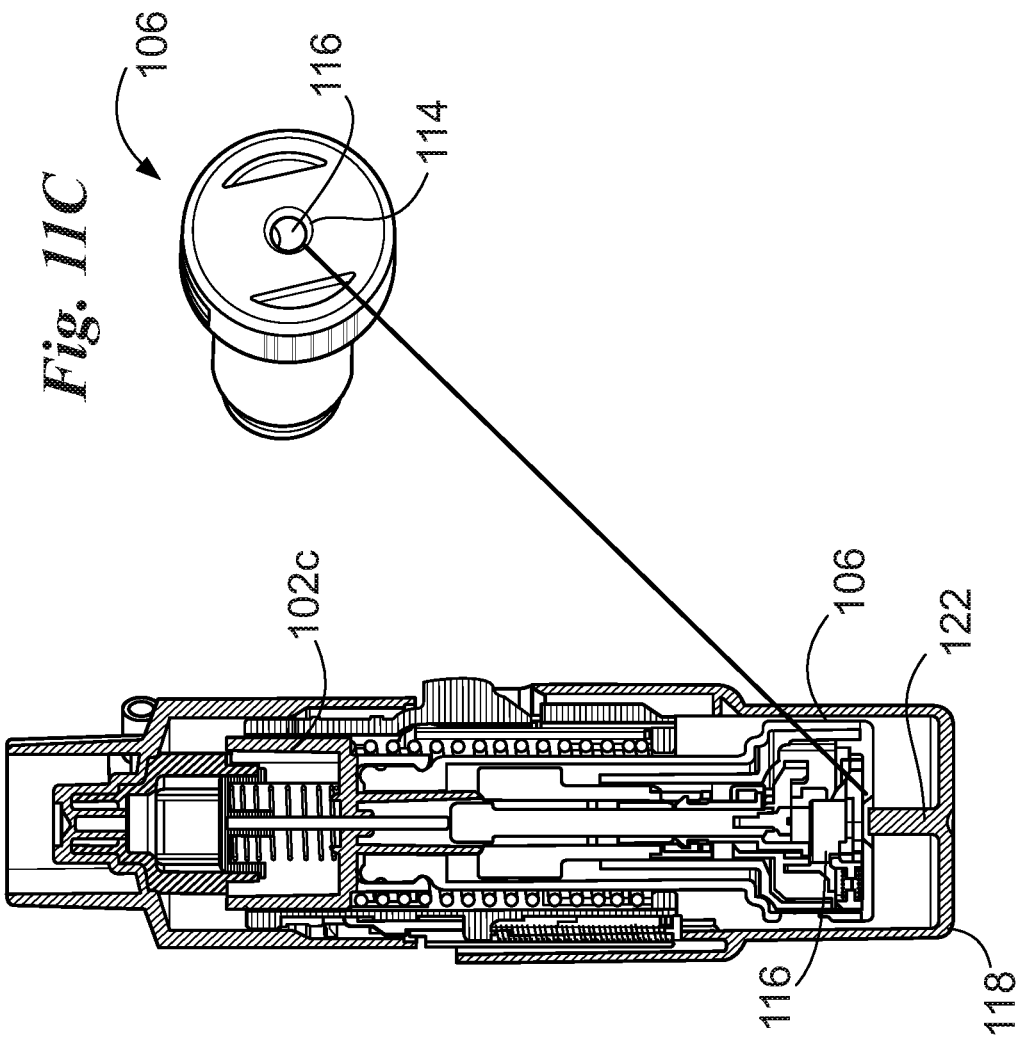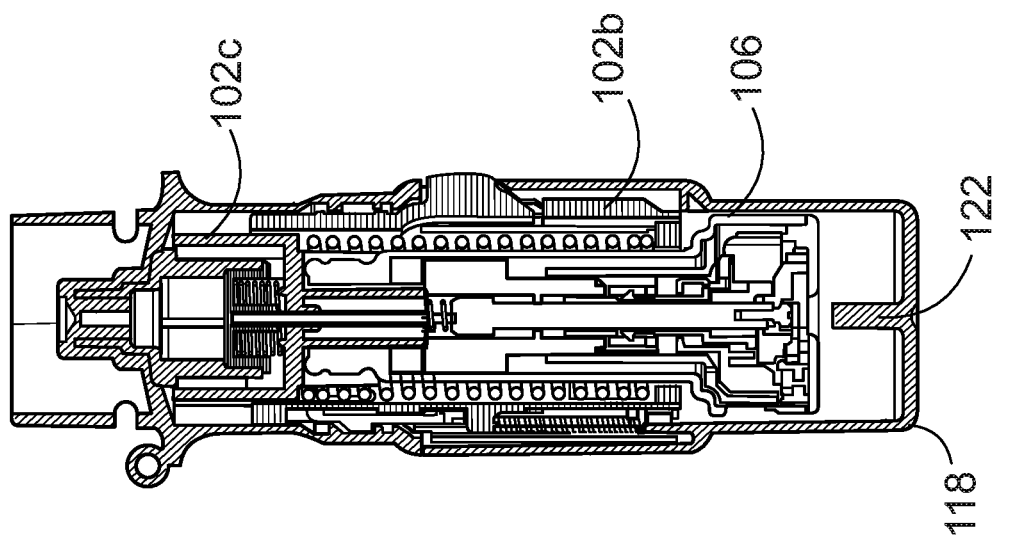

| Step | Hole Status | Primary Lock | Secondary Lock |
|---|---|---|---|
| Ready-to-use | Closed | Yes | Yes |
| Device locked at 135° | Semi-closed | No | Yes |
| Cartridge removed | Open | No | No |
| Cartridge reinserted | Open | No | No |
| Device reset | Closed | Yes | Yes |

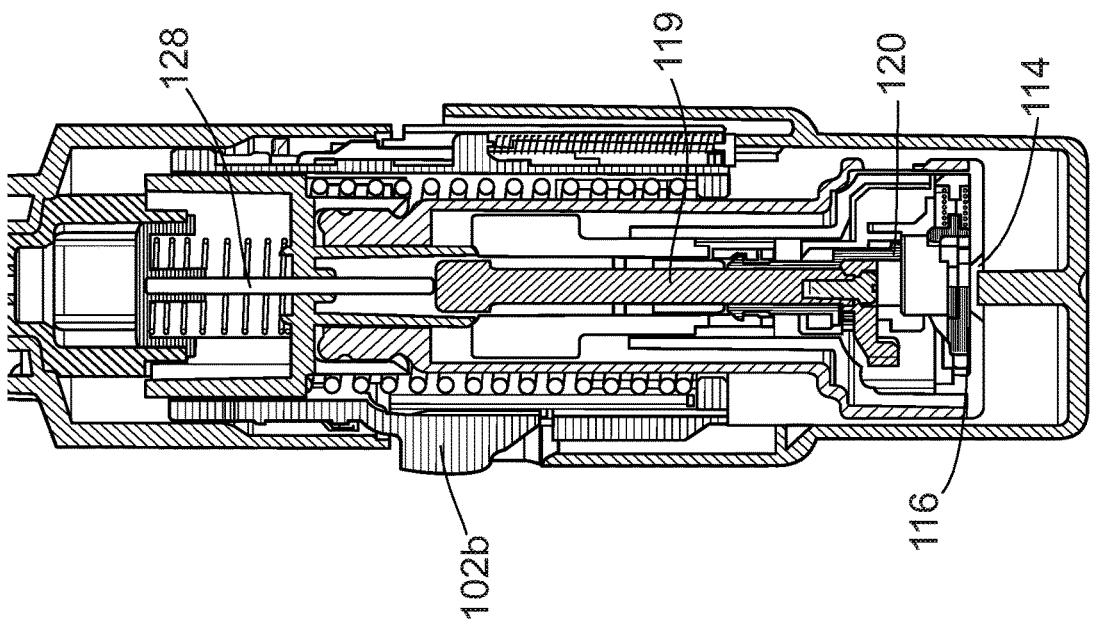
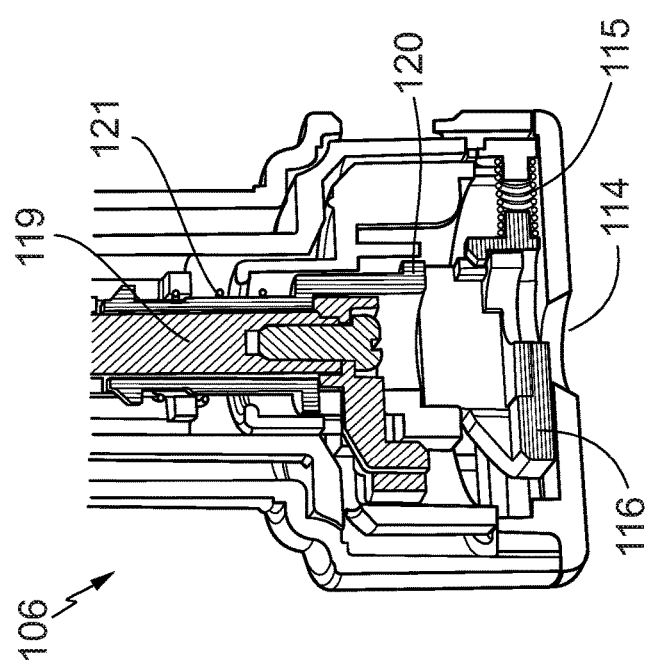

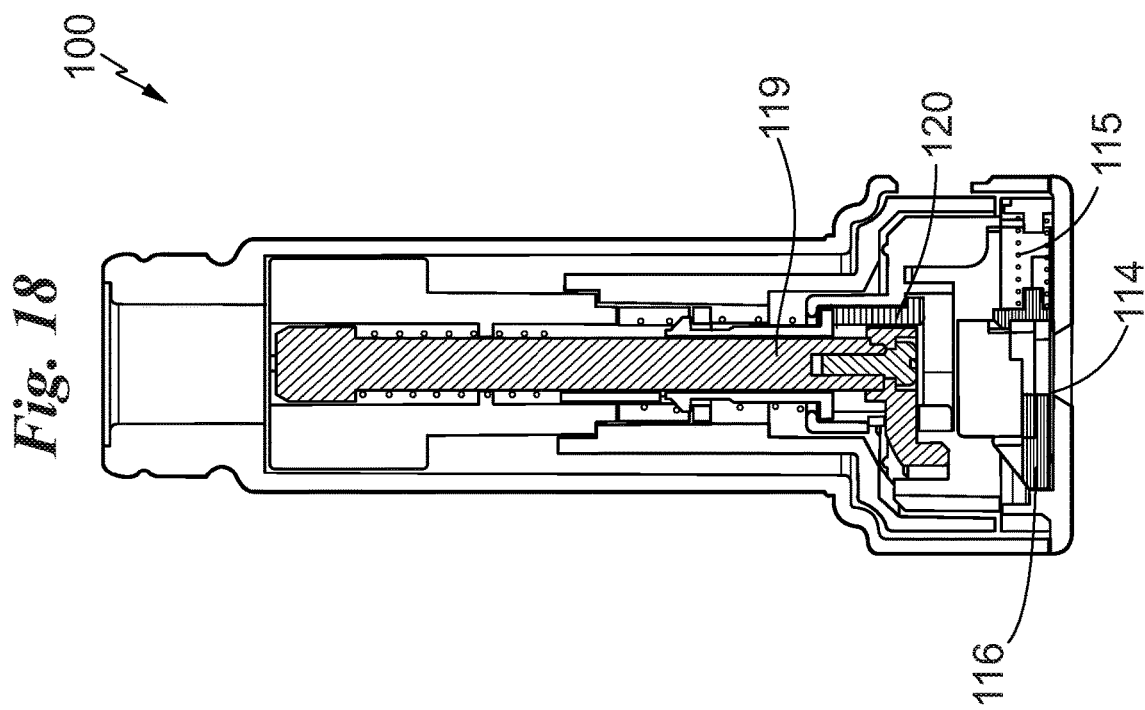
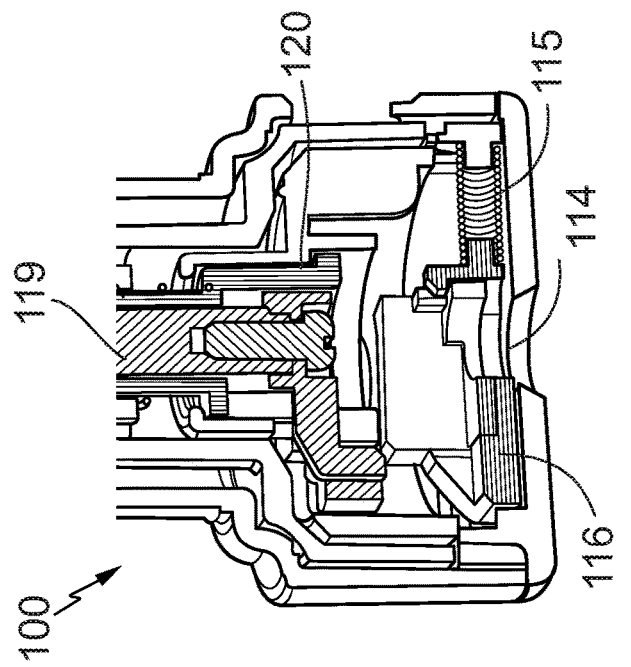

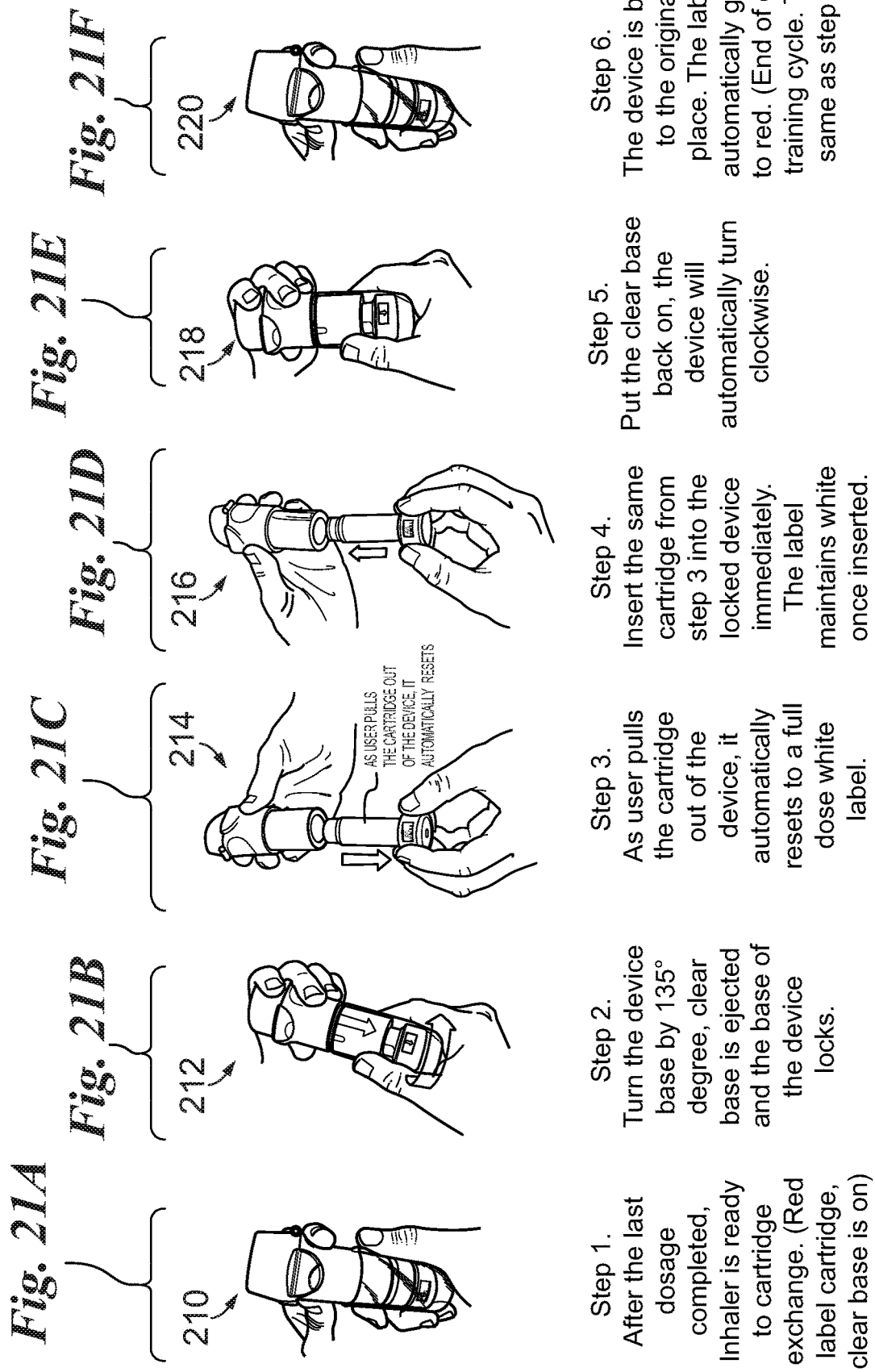

RESPIRATORY INHALER CARTRIDGE PLACEMENT TRAINING DEVICE

BACKGROUND

There are many different types of inhalers for delivery of medicament to patients on the market. These inhalers include soft mist inhalers, dry powder inhalers, and metered dose inhalers. Some inhalers are multi-dose and others are single dose inhalers. Most medicaments administered by an inhaler are administered at home, by a user. As a result, care must be taken to prevent errors that may occur during use of an inhaler device by a patient in an at-home environment.

SUMMARY

In one embodiment, a resettable respiratory inhaler training device is provided herein. The resettable respiratory inhaler training device includes a device housing having an unlocked position and a locked position, the housing comprising a chamber; a cartridge for placement into the chamber, the cartridge comprising a body for insertion into the chamber and a base, said cartridge including a status indicator window to indicate a new or used cartridge, an aperture in the base and a shutter to selectively open or close the aperture; and a reset cap comprising a protrusion for interfacing with the aperture during reset of the device; wherein removal of the cartridge from the device housing changes status indicator window from used to new to reset the cartridge for a subsequent use.

In another embodiment, a method for resetting a respiratory inhaler training device is provided including placing a reset cap on a lower portion of the device housing, rotating the reset cap in a first direction relative to the device housing to release the reset cap and lock the device housing, removing the reset cap from the device, removing the cartridge from the device housing, wherein removal of the cartridge from the device housing causes a change in a status in the status indicator window from used to new, resetting the cartridge for a subsequent use; reinserting the cartridge into the device housing, the status indicator window changes to used; replacing the reset cap onto the cartridge; and rotating the reset cap in a second direction relative to the device housing to reset the device to an unlocked and ready to use position.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIGS. 1A-1E include cross sectional views of a resettable respiratory inhaler training device embodiment, during use.

FIG. 2A is a partial sectional view of a cartridge embodiment.

FIG. 2B is a side view of the cartridge embodiment in FIG. 2A.

FIG. 2C is a bottom view of the cartridge embodiment in FIG. 2A.

FIG. 3A is a partial sectional view of a cartridge embodiment.

FIG. 3B is a side view of the cartridge embodiment in FIG. 3A.

FIG. 3C is a bottom view of the cartridge embodiment in FIG. 3A.

FIG. 4A is a partial sectional view of a cartridge embodiment.

FIG. 4B is a side view of the cartridge embodiment in FIG. 4A.

FIG. 4C is a bottom view of the cartridge embodiment in FIG. 4A.

FIG. 5A is a partial sectional view of a cartridge embodiment.

FIG. 5B is a side view of the cartridge embodiment in FIG. 5A.

FIG. 5C is a bottom view of the cartridge embodiment in FIG. 5A.

FIG. 6A is a partial sectional view of a cartridge embodiment.

FIG. 6B is a side view of the cartridge embodiment in FIG. 6A.

FIG. 6C is a bottom view of the cartridge embodiment in FIG. 6A.

FIGS. 8A-8B include cross sectional views of an upper portion of the device housing.

FIG. 11A is a cross sectional view of an embodiment of the device in an unlocked position.

FIG. 11B is a cross sectional view of an embodiment of the device shown in FIG. 11A in a locked position.

FIG. 11C is a bottom end view of a cartridge embodiment, shown in the device of FIG. 11B.

FIG. 15 is a partial sectional cross-section of a cartridge embodiment, wherein the primary lock is disengaged, and the secondary lock is engaged.

FIG. 16 is a cross-sectional view of a device embodiment including the cartridge of FIG. 15, wherein the primary lock is disengaged and the secondary lock is engaged.

FIG. 17 is a partial sectional cross-section of a cartridge embodiment, wherein the primary lock is disengaged, and the secondary lock is disengaged, releasing the shutter to unobstruct the aperture when the cartridge is removed from the device.

FIG. 18 is a cross-sectional view of the cartridge of FIG. 17, with the aperture unobstructed, and the cartridge in a reset position.

FIG. 21 includes a number of steps showing a method replacement and reset of a cartridge of a respiratory inhaler training device and reset of the device for a subsequent use.

DETAILED DESCRIPTION

Figure 1C:
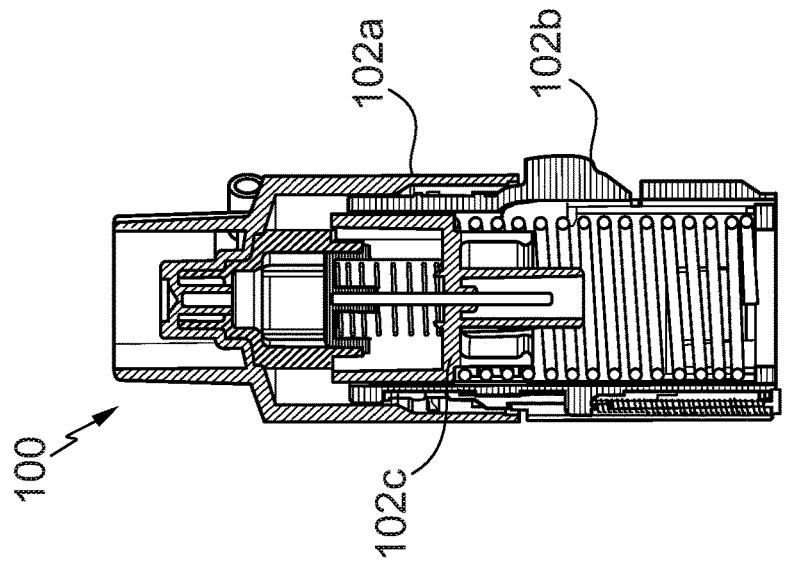

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

As used herein, the terms "subject", "user" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

Inhaler devices typically require removal and replacement of a medicament cartridge into the device prior to use for delivery of medicament. In some inhaler devices, the cartridge may include more than one dose of medicament. Once the cartridge is depleted of medicament, the user must remove the used cartridge and replace it with a new cartridge. Numerous mistakes are made in the removal and replacement of the cartridge process, including: 1) failure to remove and replace the used cartridge, 2) failure to insert the new cartridge into the chamber of the device correctly, 3) failure to understand when the cartridge has been depleted of medicament and must be replaced, among others. These issues may be corrected by training users on 1) when the cartridge is used and needs replacing, 2) how to correctly remove the cartridge, and 3) how to correctly insert a new cartridge.

Consequently, the inventors herein have discovered novel device and method embodiments for training a user on use of an inhaler device. In some embodiments, a reusable training device housing, and a removable, reusable, resettable cartridge is provided for training a user to properly remove and replace a cartridge in an inhaler device. Feedback is provided to a user during the steps of the use of the training device, including visual, tactile and audible feedback. A user is prompted to remove and replace a cartridge based on this feedback and is provided positive feedback in the form of visual and tactile signals once correctly removed (cartridge reset), once the cartridge is correctly replaced into the device, and finally once the device has been reset. The repeatability of the training facilitates effective learning for the user to ensure correct operation of the medicament-containing inhaler device. In some inhaler devices, the cartridge may include a multi-use cartridge with multiple, independent doses of medicament within one cartridge. Therefore, indication must be provided to a user when removal and replacement of the multi-use cartridge is required. The training device provided herein indicates to a user when removal is required, in one example by indication via a status window. Repeatability of the correct removal and replacement of the cartridge, and simulation of the manner in which an inhaler device functions with regard to removal and replacement of a medicament containing cartridge is provided in the device embodiments herein to effectively train a user. Consequently, reset of the cartridge is necessary to allow the training device to reuse the same cartridge at the termination of a training session. The training device may be used to simulate single use or multi-use medicament-containing cartridges in non-limiting embodiments.

Figure 1B:
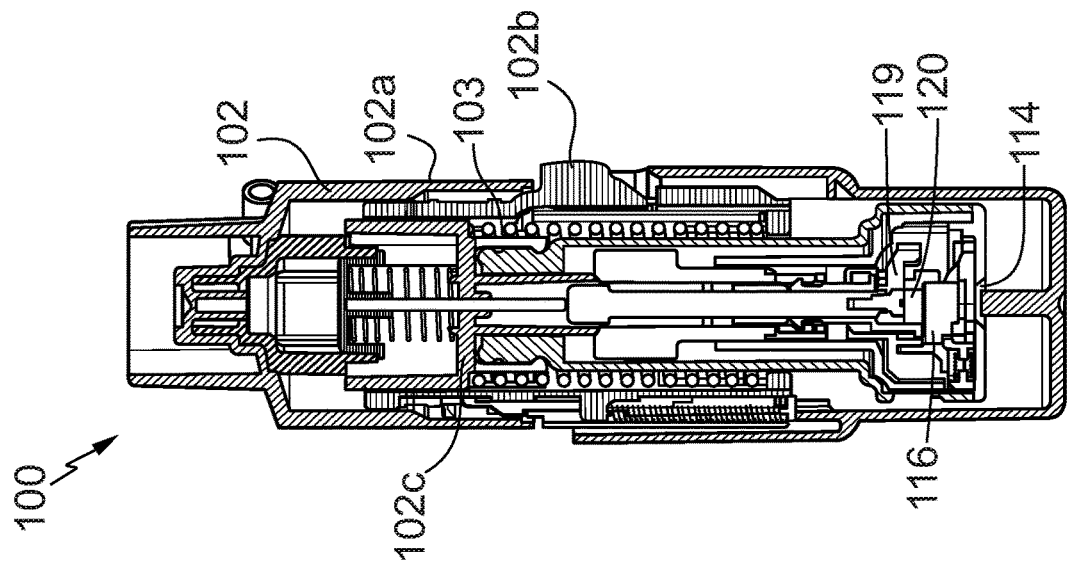

Turning to the drawings, in one embodiment, as shown in FIG. 1A-1E, a resettable respiratory inhaler training device 100 is provided. The resettable respiratory inhaler training device 100 includes a device housing 102 having an upper portion 102a, a lower portion 102b and an inner portion 102c, and a number of states including an unlocked position and a locked position. The housing includes a chamber 104, a cartridge 106 for placement into the chamber 104, the cartridge 106 including a body 108 (see FIG. 2B) for insertion into the chamber 106 and a base 110. The cartridge 106 includes a primary lock 119, and a secondary lock 120 for controlling a shutter 116. The shutter 116 interfaces with an aperture 114, and is positioned in one embodiment, in the base 110 of the cartridge 106. The shutter 116 selectively opens and closes the aperture 114 as will be described in more detail in FIGS. 2-6. The device 100 further includes a reset cap 118, which interacts with the lower portion of the device housing 102b, and is rotatable relative to the upper portion 102a along with the lower portion 102b. The reset cap 118 interfaces with the lower portion 102b to rotate the lower portion 102b in a first direction for removal of the cap 118, in one non-limiting embodiment, wherein the inner portion 102c moves toward the distal end of the device as shown in FIG. 1B under the pressure of inner portion spring, providing extension of the cartridge 106 from the device 100 to allow removal thereof. The reset cap 118 interfaces with the lower portion 102b to rotate the lower portion 102b in a second direction, following replacement of the cartridge 106 within the chamber 104, to reset the device 100. In another non-limiting embodiment, the device 100 may be provided without a reset cap 118, and the device 100 may be resettable by rotating one or more portions of the device, for example, by rotating the lower portion 102b of the device housing. In further non-limiting embodiments, new cartridges may be used with the device 100, the cartridges may be reusable or disposable.

The lower portion 102b is also associated with a lower portion biasing member 103, extending and contracting during the stages of the use of the device as shown in FIGS. 1A-1E. The biasing member 103 is in an extended position in a ready to use device position of the device 100 shown in FIG. 1A and is contracted in the locked position in FIG. 1B, as shown, upon reset of the device 100. The biasing member 103 is re-extended as shown in FIG. 1E.

Figure 1A:
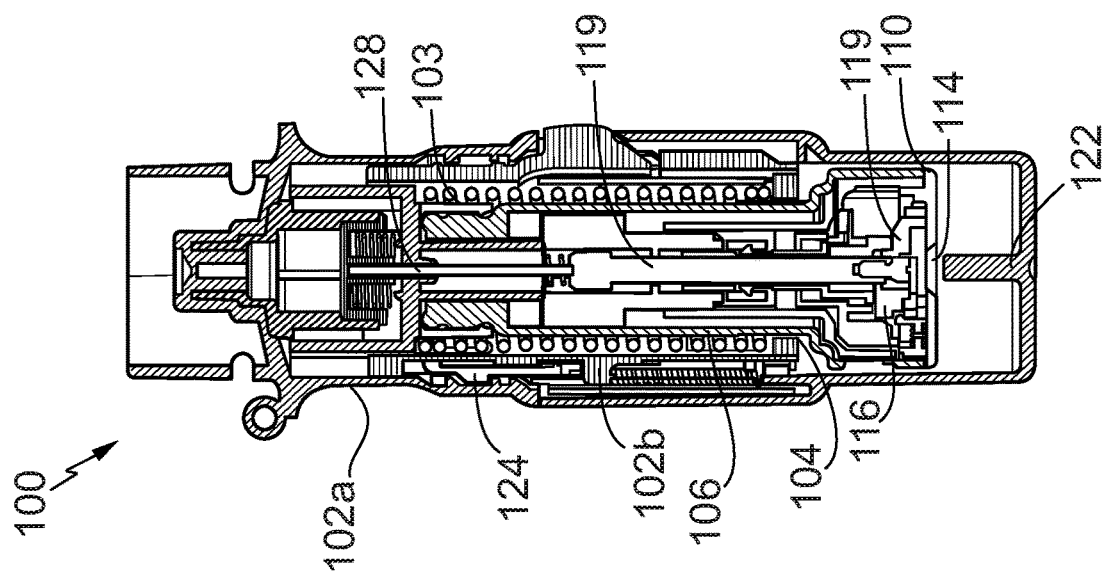
Figure 7B:
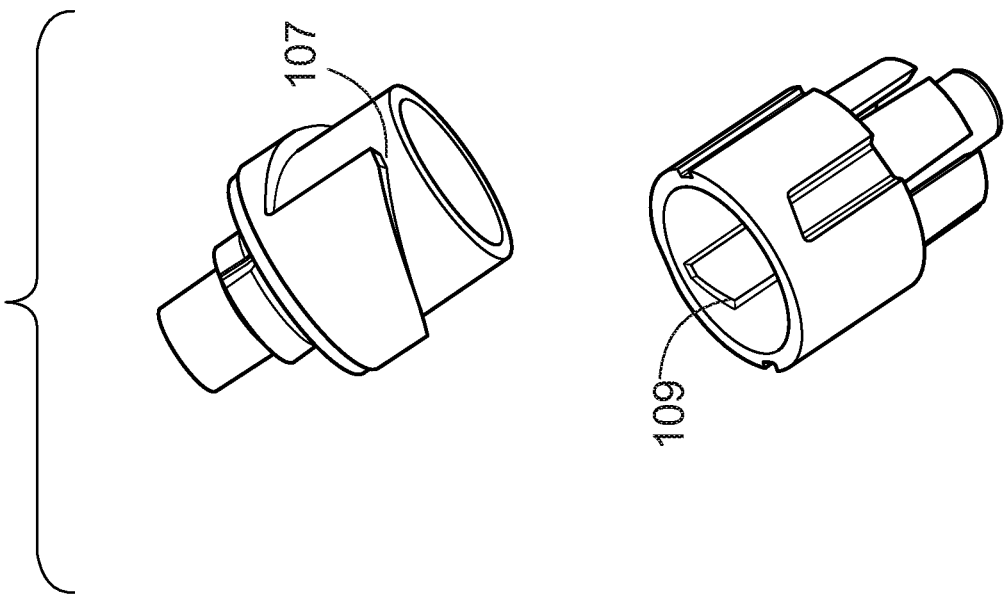
FIGS. 7A-7B includes a partial sectional view of a device housing, and an exploded view of the device housing.
Figure 7A:
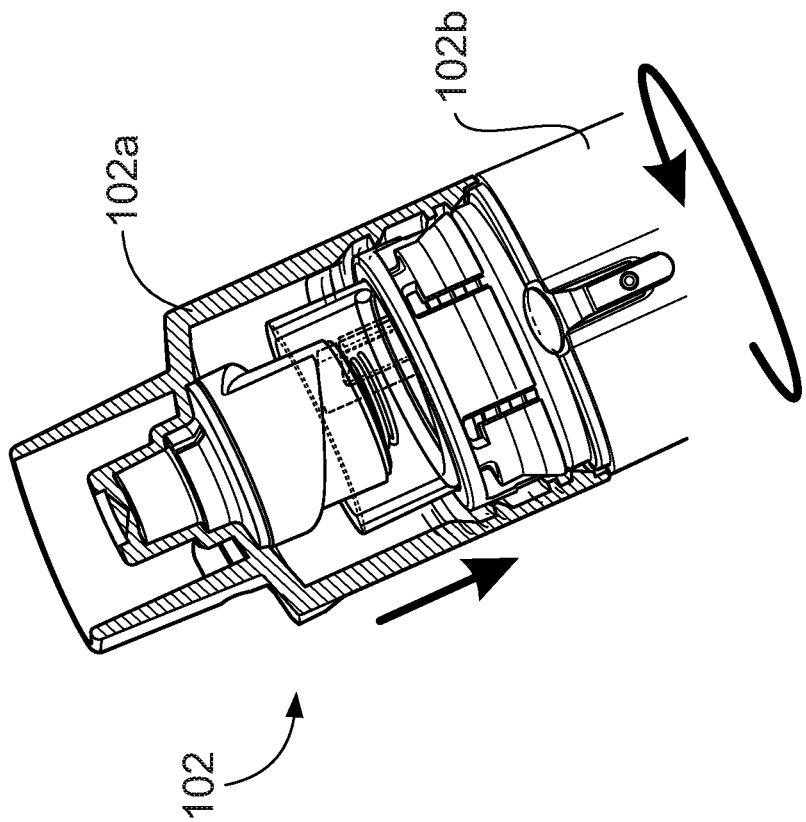

Rotation of the lower portion 102b via the reset cap 118 in a first direction to lock the device as shown from FIG. 1A-FIG. 1B causes radial movement of the lower portion 102b and linear movement of the upper portion 102a (as shown in FIGS. 7A-7B). Rotation of the lower portion 102b during reset by rotation of the cap coupled to the lower portion 102b, in one embodiment, causes the upper portion 102a to interface with the inner portion 102c as shown in FIG. 7B, wherein an upper interfacing portion (ramp) 107 interfaces with a ramp (lower interfacing portion 109) on the inner portion 102c shown in FIG. 7B. This causes movement of a locking element 124, which serves to lock the positions of the upper portion 102a and lower portion 102b relative to one another. On a portion of the upper portion 102a, a number of ridges are provided, the locking element 124 is rotatable relative to these ridges during rotation of the lower portion 102b relative to the upper portion 102a in the first direction. Once a the locking element 124 reaches a gap 126 (shown in FIGS. 9A-9B and 10A-10B), the locking element 124 is no longer movable in a radial manner, but may move longitudinally relative to the device 100 under a force of lock spring 147 preventing any further rotation of the lower portion 102b relative to the upper portion 102a, as the device 100 has reached its locked position as shown in FIG. 1B. This will prevent the lower portion 102b from turning backwards, and device will remain in a locked position until the lock 124 is reset.

FIG. 1B shows an interactivity between a cap protrusion 122 on the inner surface of the reset cap 118 and the aperture 114 in the cartridge base 110. Rotation of the lower portion 102b in the first direction extends the cartridge 106 from the housing 102 and extends the reset cap 118 from the device for removal of both the reset cap 118 and the cartridge 106. Removal of the cartridge from the device as shown in FIG. 1C effectively resets the cartridge 106 for a subsequent use (details of this reset are provided in FIGS. 2-6). Reinsertion of the reset cartridge 106 into the chamber 104 of the housing 102, followed by placement of the reset cap 118 over the lower portion 102b and the cartridge 106 allows for reset of the device 100 from a locked position to an unlocked position for a subsequent use as shown in FIG. 1E.

FIGS. 2A-6C show the various components of the device 100 during each stage of the use of the device 100. In FIG. 2A the cartridge 106 is shown, demonstrating the status of the cartridge when the device 100 is in a ready to use position (device not shown). FIG. 2B shows the cartridge 106 with body 108 and base 110, and a status indicator window 112 in a ready to use position. The window is shown as RED in the non-limiting example shown, indicating a used cartridge (in both the ready to use position and the device locked positions), and indicating to a user that removal and replacement of the cartridge 106 is required. In another example, the ready to use position may include a WHITE indicator window, and the device locked position may include a RED indicator window. An arrow pointing downward, showing the direction of removal of the cartridge 106 may also, or alternatively be provided in the status indicator window 112 in a non-limiting embodiment. Other indications of used or new, not shown herein, may be used in the device, including various combinations of letters, numbers, colors, lights, scents, sounds, or other indicia to alert a user when a cartridge is in a used condition and requires replacement, and to notify a user when the cartridge has been reset, and is in a new condition, ready for insertion into the device. FIG. 2C shows the shutter 116 position in the base 110 in the ready to use state of the device 100. The shutter 116 is obstructing the aperture 114, and consequently the aperture is in a closed position.

In FIGS. 3A-C, the cartridge 106 status is shown when the device 100 is in a locked position. In this position, the lower portion 102b of the device (not shown in this Figure) has been rotated in the first direction relative to the upper portion 102a in preparation for removal of the cartridge 106. FIG. 3B shows a side view of the cartridge 106, presenting the status indicator window 112, showing a "used" status. FIG. 3C provides a view of an embodiment of the bottom of the cartridge 106, showing the aperture 114 partially obstructed by the shutter 116. In one embodiment, this may be due to a series of actions that occur within the device 100 via a series of locks in the cartridge 106 which will be explained in greater detail in FIGS. 12-19. In other embodiments, when the aperture 114 is obstructed, it may be fully obstructed as shown in FIG. 2C instead of partially obstructed as shown in FIG. 3C.

FIGS. 4A-C show the cartridge in a "remove cartridge" state wherein the cartridge 106 has been removed from the device 100 (not shown). Removal of the cartridge from the device 100 causes the status indicator window 112 to change form "used" to "new", see FIG. 4B, resetting the cartridge 106 for a subsequent use. Upon removal of the cartridge 106 from the device housing 102, the aperture 114 is open and unobstructed by the shutter 116 as can be seen in FIG. 4C. As shown in FIG. 17, when the cartridge 106 is removed from the device, a cartridge inner housing 111 moves upward, toward a proximal end of the cartridge 106 as shown in FIG. 4A, which in turn disengages the secondary lock, allowing reset of the cartridge 106 by release of the shutter 116 such that it does not obstruct the aperture 114.

FIGS. 5A-5C show the cartridge 106 in a "reinsert cartridge" device state, wherein upon re-insertion of the, now reset "new" cartridge 106, the status indicator window 112 shows a "used" (shown as red) cartridge 106, and the aperture 114 remains unobstructed as shown in FIGS. 5B and 5C, respectively, in preparation for a subsequent training.

FIGS. 6A-C show the cartridge 106 when the device is in a reset and "ready to use" state. The reset cap 118 has been replaced over the cartridge 106, causing, in one example, the lower housing 102b (not shown) to rotate in the second direction relative to the upper housing 102a (not shown), unlocking the device housing 102 (not shown) in preparation for a subsequent use of the device 100.

FIGS. 7A-7B show a relationship between the upper portion 102a and the inner portion 102c of the device housing 102. The upper portion 102a includes an upper interfacing portion 107 that interfaces with the lower interfacing portion 109 on the inner portion 102c. Due to the angle of the interfacing portions 107, 109, during rotation of the lower portion 102b and inner portion 102c relative to the upper portion 102a, the lower portion 102b moves in an axial direction, and the inner portion 102c moves in both an axial and distal linear direction relative to the upper portion 102a.

FIGS. 8A-8B show movement of the lower portion 102b relative to the upper portion 102a from the ready to use position to the locked position. The locking element 124 is shown as moving in a distal direction from FIG. 8A to FIG. 8B, as the device 100 moves from an unlocked, ready to use position to a locked position. The position of the locking element 124 prevents further rotation of the lower portion 102b relative to the upper portion 102a.

Figure 9A:
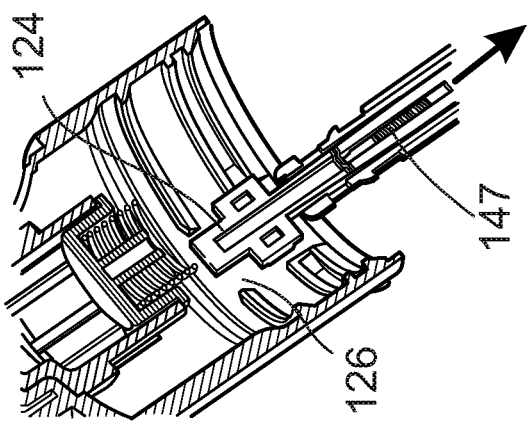
FIG. 9A is a partial sectional view of a device housing embodiment.
Figure 9B:
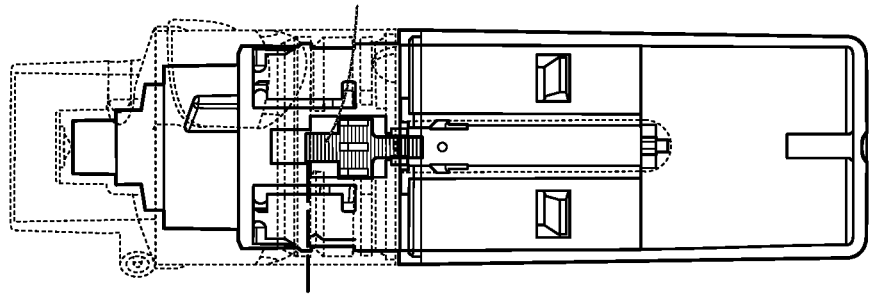
FIG. 9B is a partial sectional view of the device housing embodiment shown in FIG. 9A.
Figure 10A:
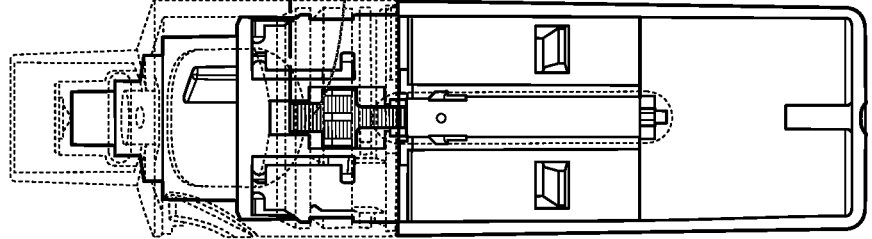
FIG. 10A is a partial sectional view of a device housing embodiment.
Figure 10B:
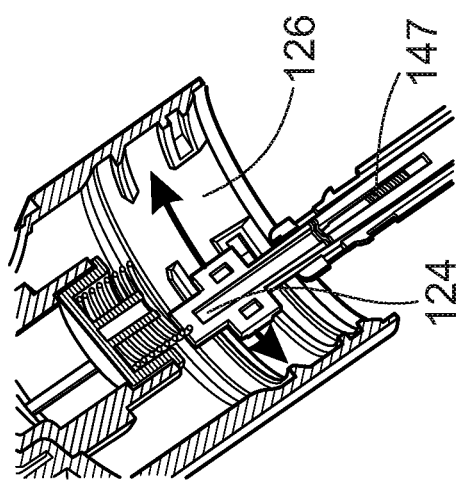
FIG. 10B is a partial sectional view of the device housing embodiment shown in FIG. 10A.

FIGS. 9A-9B show in more detail, the interactivity of the locking element 124 relative to the device housing 102. The locking element 124, when the device 100 is in an unlocked position, is rotatable relative to the device housing as shown in FIG. 9A-9B. Upon reaching a position at the device housing 102, wherein a gap 126 is provided, the locking element 124 moves longitudinally relative to the device housing in response to a force from a compressed biasing member 147 in a distal direction and can no longer move in a radial direction relative to the device 100. In this position, shown in FIG. 10A-10B, the device housing is locked.

FIGS. 11A-11C show the interactivity between the reset cap 118 and its cap protrusion 122, with the shutter 116 of the cartridge 106. Rotation of the reset cap 118 and the lower portion 102b cause the cartridge 106 to move in a distal direction in close proximity to the cap protrusion 122, while ejecting the cartridge 106 from the device housing 102. This movement causes the cap protrusion 122 to contacts the base of the cartridge 106 and/or the shutter 116, whilst the shutter 116 is obstructing the aperture 114 as can be seen in FIG. 11C. The interaction between the cap protrusion 122 and the shutter 116 causes release of the reset cap 118 from the device 100.

FIGS. 12-20 demonstrate the various stages of the cartridge 106 during use of the device 100. FIG. 12B provides a table demonstrating the positions of the locks of the cartridge 106 at each stage.

Figures 12A, 12B:
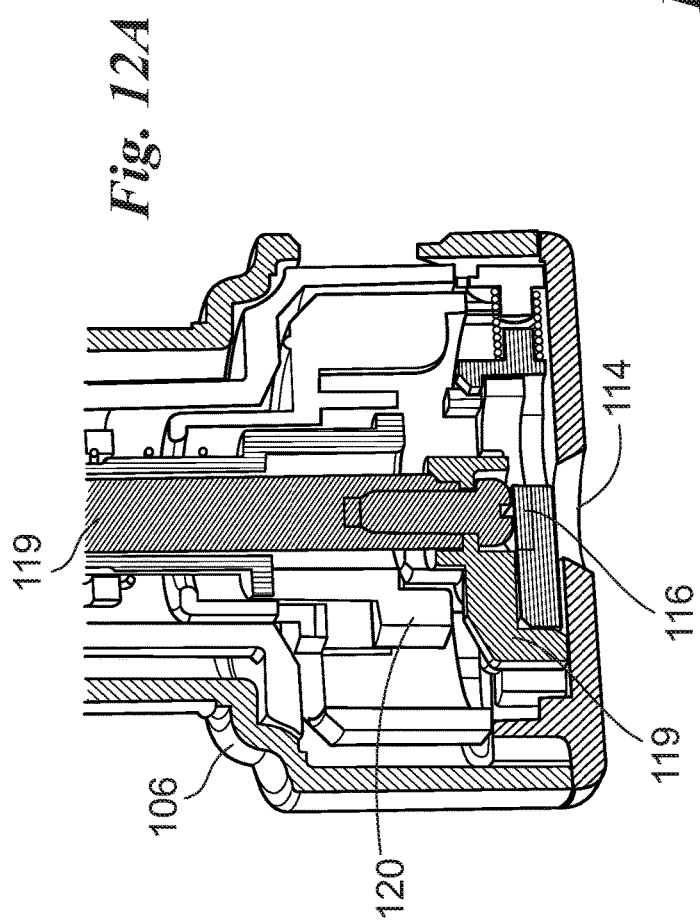
FIG. 12A is a partial sectional cross-section of a cartridge embodiment in a locked position.
FIG. 12B is a table identifying the locking features of a primary and secondary lock of the cartridge and the status of the aperture (or hole).

FIG. 12A shows the cartridge 106 when the device is in the ready to use state. The cartridge includes both a primary lock 119 and a secondary lock 120, which operate to control the movement of the shutter 116 relative to the aperture 114 during use of the device 100.

Figure 13:
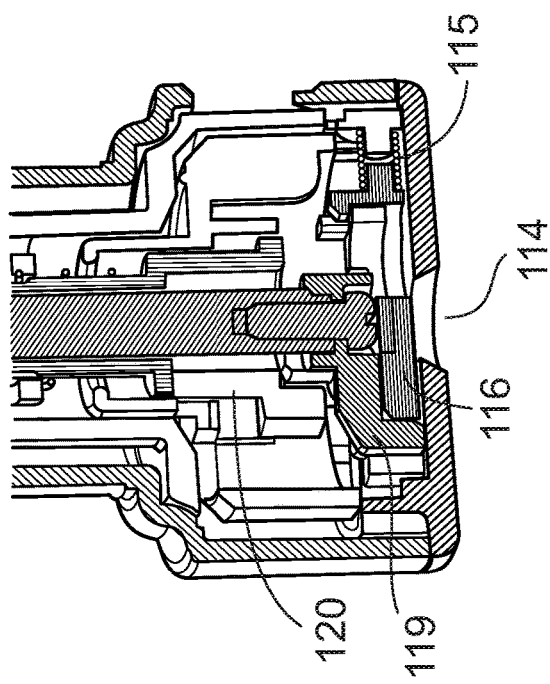
FIG. 13 is a partial sectional cross-section of a cartridge embodiment, wherein the primary and secondary locks are engaged.
Figure 14:
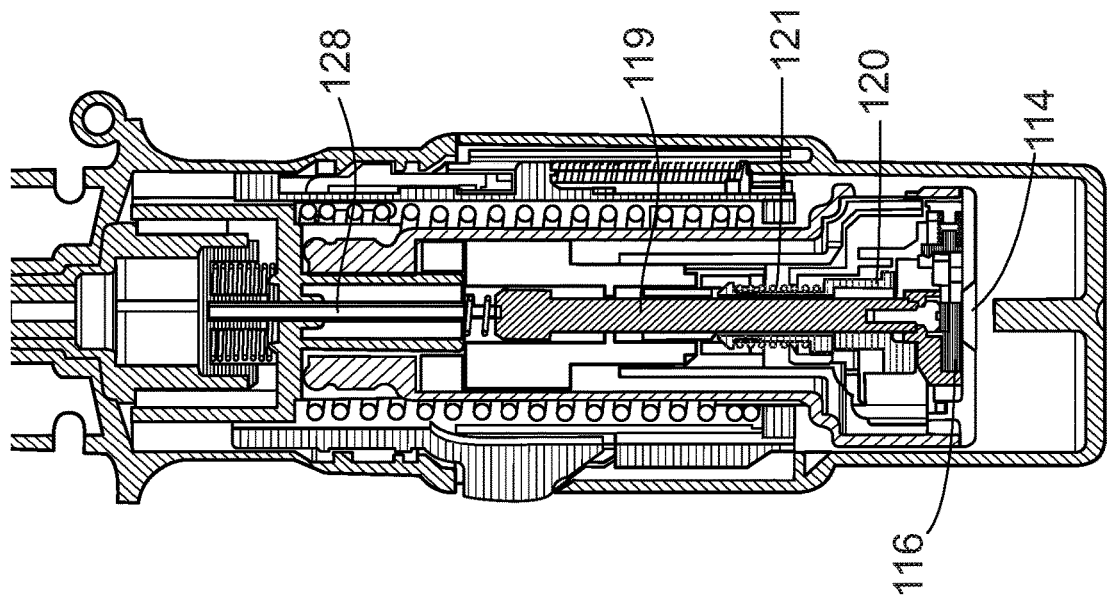
FIG. 14 is a cross-sectional view of a device embodiment including the cartridge of FIG. 13, wherein the primary and secondary locks are engaged.

FIG. 13 shows the position of the locks 119, 120 of the cartridge 106 when the device 100 is in the ready to use state. As shown in FIG. 13, both the primary 119 and the secondary 120 locks are engaged, and the shutter 116 is obstructing the aperture 114. A shutter spring 115 is biased against the shutter 116, such that once the primary and secondary locks 119, 120 are released, the aperture 114 is unobstructed. The primary lock 119 is engaged in this ready to use state of the device 100 due to contact between the rod 128 extending from the device housing 102, and the primary lock 119 as shown in FIG. 14. Rotation of the lower portion 102b causes the cartridge 106 to move in a downward linear direction removing the force on the primary lock 119 by the rod 128, releasing the primary lock 119 when the device is in the locked position.

FIG. 14 also shows a secondary lock spring 121 forcing the secondary lock 120 in a downward direction against the shutter 116, keeping the shutter 116 in a position obstructing the aperture 114.

FIG. 15 shows the cartridge 106 when the device 100 is in a locked position. The primary lock 119 has been disengaged, or released, however the secondary lock 120 is still engaged, and is maintained in the engaged position by the secondary lock spring 121 biasing against the secondary lock 120. The aperture 114 in this state remains obstructed by the shutter 116. FIG. 16 shows the device 100 in a locked position, and the cartridge 106 as shown in FIG. 15. The primary lock 119 has been disengaged, or released, due to the removal of contact between the rod 128 and the primary lock 119. The secondary lock 120 remains engaged, and the aperture 114 remains obstructed by the shutter 116.

In FIG. 17, a portion of the cartridge 106 is shown once it has been removed from the device housing 102. The primary lock 119 is disengaged and the secondary lock has been disengaged 120 upon removal of the cartridge 106 from the housing 102. Upon release of the secondary lock, the shutter spring 115 causes the shutter 116 to move to a position wherein the shutter 116 is not obstructing the aperture 114. Upon removal of the cartridge 106, the aperture is open, and the cartridge 106 is reset to a pre-use "new" cartridge position, ready for a subsequent use. FIG. 18 provides another view of the cartridge 106 in its reset state, upon its removal from the device 100.

Figure 19:
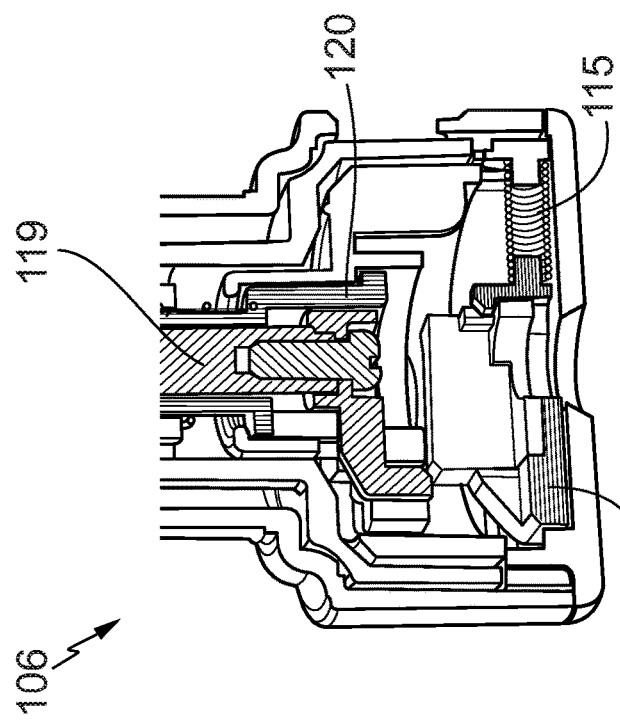
FIG. 19 is a partial sectional cross-section of a cartridge embodiment upon reinsertion of the reset cartridge into a locked device.

FIG. 19 provides a view of the reset cartridge 106 upon reinsertion into the device 100. The primary and secondary locks 119, 120 remain disengaged, and the shutter 116 remains open, against the force of the shutter spring 115.

Figure 20:
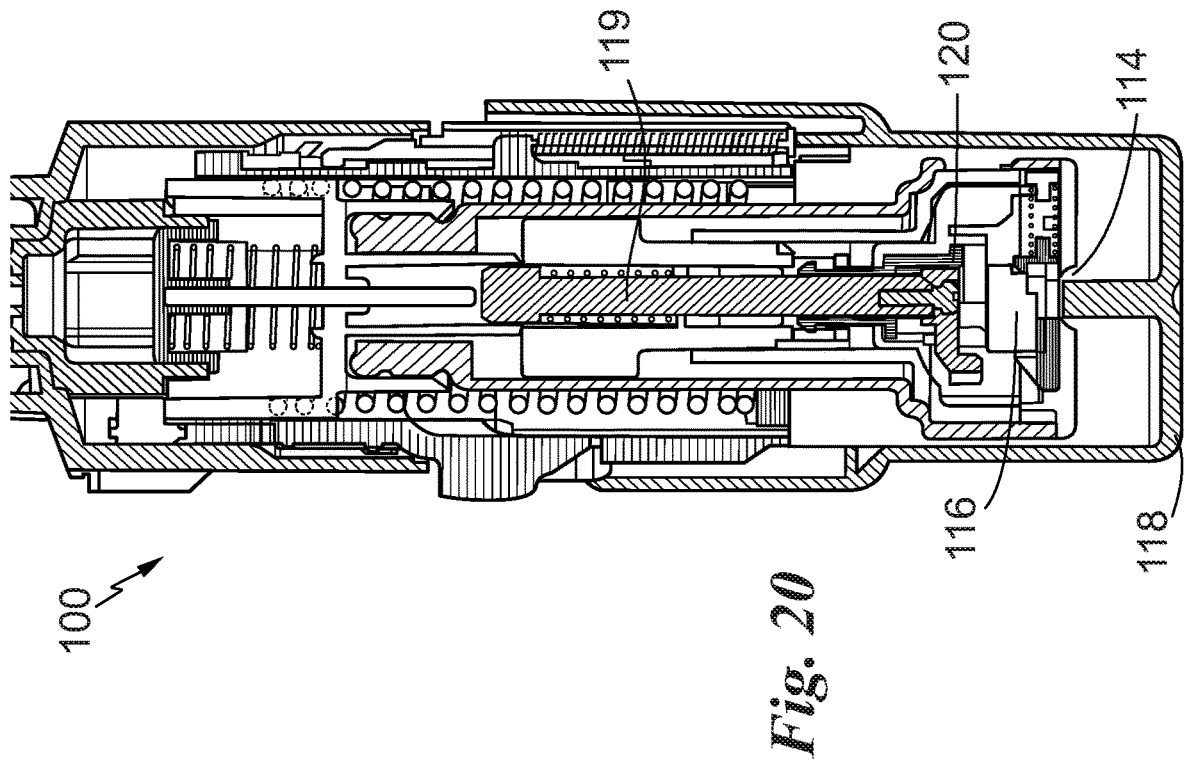
FIG. 20 is a cross sectional view of a device embodiment including the cartridge of FIG. 19.

FIG. 20 shows the device 100 including the reset cartridge 106, wherein the device 100 remains in its locked position. The reset cap 118 has been placed over the cartridge 106 in preparation for complete reset of the device 100 (i.e., reset of the device housing 102 from the locked position to the unlocked "ready to use" position). The aperture 114 remains unobstructed by the shutter 116, due to the disengagement of the primary and secondary locks 119, 120.

In another embodiment, a method 200 as shown in FIG. 21A-21F for resetting a respiratory inhaler training device 100 for a subsequent use is provided, including placing 210 a reset cap on a lower portion of the device housing, rotating 212 the reset cap in a first direction relative to the device housing to release the reset cap and lock the device housing, removing the reset cap from the device, removing the cartridge 214 from the device housing, wherein removal of the cartridge from the device housing causes a change in a status in the status indicator window from used to new, resetting the cartridge for a subsequent use; and reinserting 216 the cartridge into the device housing. The status indicator window remains new until inserted whereinafter the status indicator window changes to used; replacing 218 the reset cap onto the cartridge; and rotating 220 the reset cap and the lower portion in a second direction relative to the device housing to reset the device to an unlocked and ready to use position. Rotation of the lower portion and the reset cap occurs automatically upon replacement of the reset cap onto the device housing, in some non-limiting embodiments, due to a biasing member force rotating the lower portion in the second direction for full reset of the device 100. A further method embodiment includes training a user to correctly replace a cartridge of an inhaler device.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A resettable respiratory inhaler training device, comprising;
   a device housing comprising an unlocked position and a locked position, the housing comprising a chamber;
   a cartridge for placement into the chamber, the cartridge comprising a body and a base, wherein the body is receivable within the chamber, said cartridge comprises a status indicator window to indicate a new or used status of the cartridge, an aperture in the base of the cartridge, and a shutter to selectively open or close the aperture; and
   a reset cap comprising a protrusion for interfacing with the aperture during reset of the device;
   wherein removal of the cartridge from the device housing changes the status in the indicator window from the used status to the new status and resets the cartridge for a subsequent use.

2. The resettable respiratory inhaler training device of claim 1, wherein the device housing comprises an upper portion and a lower portion, wherein the device housing lower portion is rotatable relative to the upper portion.

3. The resettable respiratory inhaler training device of claim 2, further comprising a biasing member associated with the lower portion of the device housing, for rotating the lower portion in a second direction, unlocking and resetting the device for a subsequent use.

4. The resettable respiratory inhaler training device of claim 2, wherein the upper portion comprises an upper interfacing surface, and the lower portion comprises a lower interfacing surface, wherein the upper and lower interfacing surfaces interface upon rotation of the lower portion relative to the upper portion during removal of the cartridge.

5. The resettable respiratory inhaler training device of claim 4, wherein the interface between the upper and lower interfacing surfaces causes radial movement of the lower portion.

6. The resettable respiratory inhaler training device of claim 1, wherein rotation of the reset cap in a first direction on the device housing rotates the lower portion in the first direction, extends the cartridge from the chamber and ejects the reset cap from the device housing.

7. The resettable respiratory inhaler training device of claim 6, wherein upon removal of the cartridge from the device housing, the aperture is open.

8. The resettable respiratory inhaler training device of claim 1, wherein prior to removal of the cartridge from the device housing, the aperture is partially obstructed.

9. The resettable respiratory inhaler training device of claim 7, wherein rotation of the reset cap on the device in a second direction rotates the second portion, and resets the device to an unlocked position.

10. The resettable respiratory inhaler training device of claim 1, wherein the cartridge comprises a primary lock and a secondary lock.

11. The resettable respiratory inhaler training device of claim 10, wherein when the primary and secondary locks are engaged, the aperture is partially obstructed.

12. The resettable respiratory inhaler training device of claim 10, wherein when the primary lock is released and the secondary lock is engaged, the aperture is partially obstructed.

13. The resettable respiratory inhaler training device of claim 10, wherein when the primary lock is released and the secondary lock is released, the aperture is open.

14. The resettable respiratory inhaler training device of claim 6 wherein rotation of the lower portion in the first direction releases the primary lock.

15. The resettable respiratory inhaler training device of claim 1, wherein removal of the cartridge releases the secondary lock.

16. A method for resetting the respiratory inhaler training device of claim 1, comprising:
   placing a reset cap on a lower portion of the device housing, comprising an upper portion and lower portion wherein the lower portion is rotatable relative to the upper portion;
   rotating the reset cap and lower portion of the housing in a first direction relative to the upper portion of the device housing to release the reset cap, extend the cartridge from the chamber, and lock the device housing;
   removing the reset cap from the device;
   removing the cartridge from the device, wherein removal of the cartridge causes a change of a status in the status indicator window from used to new, resetting the cartridge;
   reinserting the cartridge into the device housing changing the status indicator window to used;
   replacing the reset cap onto the cartridge;
   rotating the reset cap and lower portion of the device housing in a second direction relative to the upper portion to reset the device to an unlocked position for a subsequent training.

17. The method of claim 16, wherein a biasing member rotates the lower portion relative to the upper portion.

18. A method for training a user to replace a cartridge of a respiratory inhaler device, comprising:
   placing a reset cap on a lower portion of the respiratory inhaler training device of claim 1, wherein the housing comprises an upper portion and lower portion wherein the lower portion is rotatable relative to the upper portion;
   rotating the reset cap and lower portion of the housing in a first direction relative to the upper portion of the device housing to release the reset cap, extend the cartridge from the chamber, and lock the device housing;
   removing the reset cap from the device;
   removing the cartridge from the device, wherein removal of the cartridge causes a change of a status in the status indicator window from used to new, resetting the cartridge;
   reinserting the cartridge into the device housing changing the status indicator window to used;
   replacing the reset cap onto the device;
   rotating the reset cap and lower portion of the device housing in a second direction relative to the upper portion to reset the device to an unlocked position for a subsequent training.

19. The method of claim 18, wherein a biasing member rotates the lower portion relative to the upper portion.

\* \* \* \* \*